(12) United States Patent
Ikeda et al.

(10) Patent No.: US 11,718,841 B2
(45) Date of Patent: Aug. 8, 2023

(54) METHOD FOR PRODUCING GALACTOOLIGOSACCHARIDE

(71) Applicant: KABUSHIKI KAISHA YAKULT HONSHA, Tokyo (JP)

(72) Inventors: Masakazu Ikeda, Tokyo (JP); Masahiko Ito, Tokyo (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 0 days.

(21) Appl. No.: 17/559,121

(22) Filed: Dec. 22, 2021

(65) Prior Publication Data

US 2022/0112533 A1    Apr. 14, 2022

Related U.S. Application Data

(62) Division of application No. 16/628,163, filed as application No. PCT/JP2018/024078 on Jun. 26, 2018, now abandoned.

(30) Foreign Application Priority Data

Jul. 4, 2017 (JP) .............................. JP2017-130761

(51) Int. Cl.
*C12N 9/26* (2006.01)
*C12P 19/04* (2006.01)
*C12N 9/38* (2006.01)
*C12P 19/14* (2006.01)
*C12P 19/18* (2006.01)

(52) U.S. Cl.
CPC ............ *C12N 9/2471* (2013.01); *C12P 19/04* (2013.01); *C12P 19/14* (2013.01); *C12Y 302/01023* (2013.01); *C12P 19/18* (2013.01)

(58) Field of Classification Search
CPC .................................................. C12N 9/2471
See application file for complete search history.

(56) References Cited

FOREIGN PATENT DOCUMENTS

| CN | 105274166 A | 1/2016 |
|---|---|---|
| JP | 62-79791 | 4/1987 |
| JP | 5-22517 | 3/1993 |
| JP | 2001-245690 | 9/2001 |
| RU | 2622078 C1 * | 6/2017 |
| WO | WO-2017120678 A1 * | 7/2017 ............ A21D 8/047 |

OTHER PUBLICATIONS

English Translation of RU 2 622 078. retrieved on Sep. 22, 2022.*
Kim et al., "A new kinetic model of recombinant β-galactosidase from *Kluyveromyces lactis* for both hydrolysis and transgalactosylation reactions," *Biochemical and Biophysical Research Communications*, 316 (2004) 738-743.
Extended European Search Report issued in European Patent Application No. 18828415.2 dated Mar. 5, 2021.
Written Opinion issued in Singapore Patent Application No. 11202000020R dated Jan. 27, 2021.
Search Report issued in Singapore Patent Application No. 11202000020R dated Jan. 27, 2021.
Splechtna, B. et al., "Process development for the production of prebiotic galacto-oligosaccharides from lactose using β-galactosidase from *Lactobacillus* sp." *Biotechnology Journal*, Apr. 4, 2007, vol. 2, No. 4, pp. 480-485 p. 481: Section 2.2; p. 482: Section 2.8; Fig. 5.
Hernandez- Hernandez, O. et al, "Effect of Prebiotic Carbohydrates on the growth and tolerance of Lactobacillus", Food Microbiology, Academic Press Ltd., London, GB, vol. 30, No. 2, Dec. 1, 2011, pp. 355-361.
Arreola, Sheryl Lozel et al. "Two β-Galactosidases from the Human Isolate Bifidobacterium breve DSM 20213: Molecular Cloning and Expression, Biochemical characterization and Synthesis of Galacto-Oligosaccharides", PLOS One, vol. 9, Issue 8, Aug. 4, 2014, p. e104056
Montilla et al., "*Effects of monovalent cations (Na+ and K ) on galactooligosaccharides production during lactose hydrolysis by Kluyveromyces lactis B-galactosidase*— '3.3 Influence of sodium-magnesium interaction'", Michwissenschaft, vol. 67, ISSN 0026-3788, in particular abstract, 2012, pp. 14-18.
Official Communication issued in International Bureau of Wipo Patent Application No. PCT/JP2018/024078, dated Aug. 14, 2018.

* cited by examiner

*Primary Examiner* — Yong D Pak
(74) *Attorney, Agent, or Firm* — Greenblum & Bernstein, P.L.C.

(57) ABSTRACT

Provided is a method for improving the production amount of a tri- or higher galactooligosaccharide and the reaction rate by a method for producing a galactooligosaccharide characterized by allowing β-galactosidase to react with a substrate in the presence of 5 to 60 mM sodium ions and 0.5 to 8 mM magnesium ions.

11 Claims, No Drawings

METHOD FOR PRODUCING GALACTOOLIGOSACCHARIDE

CROSS-REFERENCE TO RELATED APPLICATIONS

The present application is a divisional of U.S. patent application Ser. No. 16/628,163 filed Jan. 2, 2020, which is a U.S. National Stage Application of International Patent Application No. PCT/JP2018/024078 filed Jun. 26, 2018, which claims the benefit of Japanese Patent Application No. 2017-130761 filed Jul. 4, 2017. The disclosure of each of the above-noted applications is expressly incorporated herein by reference in its entirety.

TECHNICAL FIELD

The present invention relates to a method for producing a galactooligosaccharide using β-galactosidase, more particularly relates to a method for improving the production amount of a tri- or higher galactooligosaccharide and the reaction rate by allowing β-galactosidase to act on a substrate in the coexistence of specific metal ions at a predetermined concentration.

BACKGROUND ART

β-Galactosidase is known to catalyze a transgalactosylation reaction as well as a hydrolysis reaction of a β-D-galactoside bond in lactose or the like, and is used in the production of a galactooligosaccharide that selectively allows Bifidobacteria to grow in the intestine.

A method for improving a transgalactosylation ratio in such a reaction using β-galactosidase has been studied. For example, a method for increasing the transgalactosylation ratio by increasing the concentration of lactose serving as a substrate and allowing β-galactosidase to act thereon has been proposed (PTL 1).

A product obtained by a transgalactosylation reaction using β-galactosidase can include, other than tri- or higher galactooligosaccharides such as β-D-galactopyranosyl-(1-4) β-D-galactopyranosyl-D glucose (4'-GL), for example, transgalactosylated disaccharides such as β-D-galactopyranosyl (1-6)-D-glucose, however, from the viewpoint of improvement of an effect of promoting the growth of Bifidobacteria or the like, a technique for further increasing the production amount of a tri- or higher galactooligosaccharide has been demanded. Further, from the viewpoint of reduction of the production cost and improvement of the production efficiency, it is important to reduce a reaction time until the production amount of a tri- or higher galactooligosaccharide reaches the maximum, and a method for improving the reaction rate has been awaited.

CITATION LIST

Patent Literature

PTL 1: JP-B-5-22517

SUMMARY OF INVENTION

Technical Problem

An object of the present invention is to provide a method for improving the production amount of a tri- or higher galactooligosaccharide and the reaction rate in a method for producing a galactooligosaccharide using β-galactosidase.

Solution to Problem

The present inventors conducted intensive studies for achieving the above object, and as a result, they found that by allowing β-galactosidase to react with a substrate in the presence of sodium ions and magnesium ions within a specific concentration range, the production amount of a tri- or higher galactooligosaccharide can be increased, and also the reaction time until the production amount reaches the maximum can be reduced, and thus completed the present invention.

That is, the present invention is directed to a method for producing a galactooligosaccharide, characterized by allowing β-galactosidase to react with a substrate in the presence of 5 to 60 mM sodium ions and 0.5 to 8 mM magnesium ions.

Advantageous Effects of Invention

According to the production method of the present invention, the production amount of a tri- or higher galactooligosaccharide can be increased, and also the reaction rate is improved, so that the reaction time until the maximum production amount is reached can be reduced. Therefore, a tri- or higher galactooligosaccharide can be efficiently produced at low cost.

DESCRIPTION OF EMBODIMENTS

The method for producing a galactooligosaccharide of the present invention is characterized by allowing β-galactosidase to react with a substrate in the presence of 5 to 60 mM sodium ions and 0.5 to 8 mM magnesium ions. In the galactooligosaccharide, a tri- or higher galactooligosaccharide represented by the general formula: Gal-(Gal)n-Glc (wherein Gal represents a galactose residue, Glc represents glucose, and n represents an integer of 1 to 6) is included.

β-Galactosidase is an enzyme that catalyzes a hydrolysis reaction of a β-galactoside bond in lactose, o-nitrophenyl-β-D-galactopyranoside, or the like, or a transgalactosylation reaction. The β-galactosidase to be used in the present invention is not particularly limited, but from the viewpoint of improvement of the production amount of a tri- or higher galactooligosaccharide and the reaction rate, one derived from a microorganism belonging to the genus *Kluyveromyces*, the genus *Streptococcus*, the genus *Lactobacillus*, the genus *Bifidobacterium*, the genus *Bacillus*, or the like is preferred, further, one derived from *Kluyveromyces lactis*, *Kluyveromyces fragilis*, *Streptococcus thermophilus*, *Lactobacillus bulgaricus*, or *Bifidobacterium breve* is preferred, particularly, β-galactosidase derived from a microorganism belonging to the genus *Kluyveromyces* is preferred, and further, β-galactosidase derived from *Kluyveromyces lactis* is preferred.

As a commercially available product of the above-mentioned β-galactosidase, for example, GODO-YNL (manufactured by GODO SHUSEI Co., Ltd.) and Maxilact LG 5000 (manufactured by DSM) derived from *Kluyveromyces lactis*, Lactozym 3000 L (manufactured by Novozymes A/S) derived from *Kluyveromyces fragilis*, Lactase Y-ST (manufactured by Yakult Pharmaceutical Industry Co., Ltd.) derived from *Streptococcus thermophilus*, and the like can be exemplified.

The form of a microorganism having β-galactosidase activity or β-galactosidase derived from the microorganism is not particularly limited, and for example, a culture solution, a cell concentrate or pellet obtained by concentration of a culture solution through centrifugation, a membrane treatment, or the like, dry cells, a cell homogenate, a crude enzyme solution, a purified enzyme solution, an enzyme powder, and the like are exemplified, and these are prepared according to a known method.

For example, when a microorganism having β-galactosidase activity is used, the microorganism is cultured according to a known method for culturing the microorganism, and the obtained culture solution is used as it is, or the culture solution is subjected to a known treatment such as centrifugation, a membrane treatment, drying, or homogenization as needed, and is used as a cell concentrate or pellet, dry cells, a cell homogenate solution, or the like. The cells may be used as living cells as such, or may be subjected to an organic solvent treatment, a lyophilization treatment, or the like and used as dead cells.

Further, when β-galactosidase derived from a microorganism having β-galactosidase activity is used, there is no particular restriction on the purification conditions or the purification degree, and a general purification method can be used. After the microorganism is cultured according to a known method, cells are separated by a separation means such as centrifugation or a membrane treatment, and when β-galactosidase is contained in the culture supernatant, the culture supernatant is recovered and can be used as a crude enzyme solution. Further, when β-galactosidase is contained in the cells, the cells are physically homogenized using a homogenizer or by a supersonic treatment, or enzymatically treated using a cell-wall digesting enzyme or the like to obtain an intracellular extract, which can be used as a crude enzyme solution. Such a crude enzyme solution may be formed into a purified enzyme solution with a high purification degree by appropriately combining an ammonium sulfate precipitation treatment, dialysis, gel filtration chromatography, ion-exchange chromatography, adsorption chromatography, affinity chromatography, and the like.

As the substrate on which the above-mentioned β-galactosidase is allowed to act, a case where it is a single substrate that acts as both an acceptor and a donor of a galactosyl group, and a case where an acceptor and a donor of a galactosyl group separately coexist are included. Examples of the substrate to serve as a donor of a galactosyl group include lactose and o-nitrophenyl-β-D-galactopyranoside. Further, examples of the substrate to serve as an acceptor of a galactosyl group include lactose, a galactooligosaccharide, glucose, and glycerol.

The concentration of the substrate is appropriately set according to the type thereof or the like, however, for example, when lactose is used, from the viewpoint of an effect of improving the production amount of a tri- or higher galactooligosaccharide and the reaction rate, the concentration thereof is preferably from 5 to 65 mass %, more preferably from 15 to 60 mass %. Further the addition amount of β-galactosidase can be appropriately adjusted according to a desired reaction time, but is preferably from 10 to 1000 U, more preferably from 30 to 800 U per gram of lactose. The reaction temperature or the like can be appropriately set according to the optimum temperature of β-galactosidase to be used, or the like. For example, when β-galactosidase derived from *Kluyveromyces lactis* is used, the reaction temperature is preferably from 30 to 50° C., more preferably from 40 to 50° C. Note that the measurement of the enzyme activity (U) is as follows.

[Measurement Method for Enzyme Activity (U) of β-Galactosidase]

0.5 mL of a diluted enzyme sample is placed in a test tube, and 0.5 mL of 100 mM $KH_2PO_4$—NaOH buffer (pH 6.5, hereinafter referred to as "buffer") to which manganese chloride is added so that the concentration becomes 0.1 mM is added thereto and mixed therewith, and then incubation is performed at 37° C. for 3 minutes. 1.0 mL of a 0.1% o-nitrophenyl-β-D-galactopyranoside (hereinafter referred to as "ONPG") solution pre-incubated at 37° C. is added thereto and immediately mixed therewith, and then incubation is performed accurately at 37° C. for 1 minute. 2.0 mL of a 0.2 M sodium carbonate solution is added thereto and immediately mixed therewith, and the reaction is stopped (a test system). Separately, 0.5 mL of a diluted enzyme sample is placed in a test tube, and 0.5 mL of the buffer is added thereto and mixed therewith, and thereafter, 2.0 mL of a 0.2 M sodium carbonate solution is added thereto, and then incubation is performed at 37° C. for 3 minutes. 0.1 mL of the ONPG solution pre-incubated at 37° C. is added thereto and mixed therewith, and then incubation is performed accurately at 37° C. for 1 minute (a blind test system). Distilled water is used as a control, and the absorbance at 420 nm of the test system and the blind test system is measured, and the enzyme activity (U) is calculated according to the following formula.

$$\text{Enzyme activity}^* = (A_1 - A_2) \times 10 \times B \quad \text{[Numerical Formula 1]}$$

$A_1$: absorbance of test system
$A_2$: absorbance of blind test system
B: dilution factor
*: U/mL In the present invention, the above-mentioned β-galactosidase is allowed to react with a substrate in the presence of sodium ions and magnesium ions. The concentration of sodium ions in the reaction system is from 5 to 60 mM. On the other hand, the concentration of magnesium ions is from 0.5 to 8 mM, more preferably from 1.5 to 8 mM. In a case where the concentration of sodium ions is more than 60 mM or a case where the concentration of magnesium ions is more than 8 mM, a load when the obtained galactooligosaccharide is purified by desalting becomes larger, and therefore, such a case is not preferred. By allowing sodium ions and magnesium ions to coexist within such a range, the production amount of a tri- or higher galactooligosaccharide and the reaction rate can be improved. Sodium ions and magnesium ions can be added to the reaction system in the form of a solid or a buffer of a salt such as a chloride, a carbonate, an acetate, or a phosphate, and sodium chloride and magnesium chloride are preferred from the viewpoint of a small change in pH after addition thereof.

In general, the transgalactosylation reaction by β-galactosidase competes with the hydrolysis reaction of a substrate, and therefore, when β-galactosidase is allowed to act on the substrate, a desired galactooligosaccharide is produced, and also a monosaccharide such as glucose or galactose is generated by the competing hydrolysis reaction, and further, the once produced galactooligosaccharide is also subjected to hydrolysis. In such a manner, the transgalactosylation reaction and the hydrolysis reaction compete with each other, and further, accompanying that, various combinations of an acceptor and a donor of a galactosyl group may occur, and therefore, it is difficult to control the reactions so that the transgalactosylation reaction between a specific acceptor and a specific donor is preferentially made to proceed so as to produce a desired galactooligosaccharide. On the other hand, in the present invention, by allowing β-galactosidase to act on the substrate in the presence of sodium ions and magnesium ions within a specific concentration range, the production amount of a tri- or higher galactooligosaccharide among the galactooligosaccharides can be increased, and moreover, the reaction rate thereof can be increased so that the time until the production amount reaches the maximum can be reduced, and thus, a tri- or higher galactooligosaccharide can be efficiently produced at low cost.

Further, the method of the present invention can also be applied to a second-order reaction in the production of a galactooligosaccharide by a consecutive reaction in which two types of β-galactosidase are allowed to act on. That is, as a first-order reaction, a microorganism having β-galactosidase activity or β-galactosidase derived from the microorganism is allowed to react with the substrate, and thereafter, as a second-order reaction, β-galactosidase different from that used in the first-order reaction is allowed to act on the first-order reaction solution in the presence of 5 to 60 mM sodium ions and 0.5 to 8 mM magnesium ions, whereby the unreacted substrate is reduced, and also the production amount of the galactooligosaccharide can be increased.

As the microorganism having β-galactosidase activity to be used in the first-order reaction, for example, a microorganism belonging to the genus *Sporobolomyces*, the genus *Aspergillus*, or the genus *Bacillus* is preferred, particularly, a microorganism belonging to the genus *Sporobolomyces* is preferred, and further, *Sporobolomyces singularis* is preferred from the viewpoint of improvement of the production amount of a tri- or higher galactooligosaccharide and the reaction rate.

The form of the microorganism having β-galactosidase activity or β-galactosidase derived from the microorganism to be used in the first-order reaction is not particularly limited, and for example, a culture solution, a cell concentrate or pellet obtained by concentration of a culture solution through centrifugation, a membrane treatment, or the like, dry cells, a cell homogenate, a crude enzyme solution, a purified enzyme solution, an enzyme powder, and the like are exemplified, and these are prepared according to a known method.

For example, when a microorganism having β-galactosidase activity is used, the microorganism is cultured according to a known method for culturing the microorganism, and the obtained culture solution is used as it is, or the culture solution is subjected to a known treatment such as centrifugation, a membrane treatment, drying, or homogenization as needed, and is used as a cell concentrate or pellet, dry cells, a cell homogenate solution, or the like. The cells may be used as living cells as such, or may be subjected to an organic solvent treatment, a lyophilization treatment, or the like and used as dead cells.

Further, when β-galactosidase derived from a microorganism having β-galactosidase activity is used, there is no particular restriction on the purification conditions or the purification degree, and a general purification method can be used. After the microorganism is cultured according to a known method, cells are separated by a separation means such as centrifugation or a membrane treatment, and when β-galactosidase is contained in the culture supernatant, the culture supernatant is recovered and can be used as a crude enzyme solution. Further, when β-galactosidase is contained in the cells, the cells are physically homogenized using a homogenizer or by a supersonic treatment, or enzymatically treated using a cell-wall digesting enzyme or the like to obtain an intracellular extract, which can be used as a crude enzyme solution. Such a crude enzyme solution may be formed into a purified enzyme solution with a high purification degree by appropriately combining an ammonium sulfate precipitation treatment, dialysis, gel filtration chromatography, ion-exchange chromatography, adsorption chromatography, affinity chromatography, and the like.

In the first-order reaction, the microorganism having β-galactosidase activity or β-galactosidase derived from the microorganism is allowed to react with the substrate such as lactose. The reaction conditions can be appropriately set according to the properties of the microorganism having β-galactosidase activity or β-galactosidase derived from the microorganism to be used. For example, when *Sporobolomyces singularis* is used as the microorganism having β-galactosidase activity and lactose is used as the substrate, from the viewpoint of the effect of improving the production amount of the galactooligosaccharide and the production rate, the concentration of lactose is preferably from 10 to 60 mass %, more preferably from 40 to 50 mass %. Further, the addition amount of *Sporobolomyces singularis* is preferably from 0.03 to 0.3 U, more preferably from 0.2 to 0.3 U per gram of lactose. Further, the reaction temperature is about 30 to 70° C., and the reaction may be performed for about 24 to 96 hours.

In the second-order reaction, β-galactosidase different from that used in the first-order reaction is allowed to act on the first-order reaction solution obtained by the first-order reaction in the presence of sodium ions and magnesium ions within a specific concentration range.

β-Galactosidase to be used in the second-order reaction is not particularly limited, however, from the viewpoint of improvement of the production amount of a tri- or higher galactooligosaccharide and the reaction rate, one derived from a microorganism belonging to the genus *Kluyveromyces*, the genus *Streptococcus*, the genus *Lactobacillus*, the genus *Bifidobacterium*, the genus *Bacillus*, or the like is preferred, further, one derived from *Kluyveromyces lactis, Kluyveromyces fragilis, Streptococcus thermophilus, Lactobacillus bulgaricus*, or *Bifidobacterium breve* is preferred, particularly, β-galactosidase derived from a microorganism belonging to the genus *Kluyveromyces* is preferred, and further, β-galactosidase derived from *Kluyveromyces lactis* is preferred.

By allowing the above-mentioned β-galactosidase to act on the first-order reaction solution in the presence of sodium ions and magnesium ions within a specific concentration range, the production amount of a tri- or higher galactooligosaccharide is increased. Further, the reaction rate thereof is also improved, and the reaction time until the production amount of a tri- or higher galactooligosaccharide reaches the maximum is reduced. The concentration of sodium ions in the second-order reaction solution is from 5 to 60 mM. On the other hand, the concentration of magnesium ions is from 0.5 to 8 mM, more preferably from 1.5 to 8 mM. In a case where the concentration of sodium ions is more than 60 mM or a case where the concentration of magnesium ions is more than 8 mM, a load when the galactooligosaccharide is desalted to be purified becomes larger, and therefore, such a case is not preferred. By allowing sodium ions and magnesium ions to exist within such a concentration range, the production amount of the galactooligosaccharide and the production efficiency can be improved. Sodium ions and magnesium ions can be added to the reaction system in the form of a solid or a buffer of a salt such as a chloride, a carbonate, an acetate, or a phosphate, and sodium chloride and magnesium chloride are preferred from the viewpoint of a small change in pH after addition thereof.

The concentration of residual lactose in the first-order reaction solution is preferably from 5 to 65 mass %, more preferably from 15 to 60 mass % from the viewpoint of an effect of improving the production amount of a tri- or higher galactooligosaccharide and the reaction rate. Further, the addition amount of β-galactosidase is preferably from 10 to 1000 U, more preferably from 30 to 800 U per gram of residual lactose. The reaction temperature or the like can be appropriately set according to the optimum temperature of β-galactosidase to be used, or the like. For example, when β-galactosidase derived from *Kluyveromyces lactis* is used, the reaction temperature is preferably from 30 to 50° C., more preferably from 40 to 50° C. from the viewpoint of an effect of improving the production amount of a tri- or higher galactooligosaccharide and the production rate.

The reaction solution in which the galactooligosaccharide is produced as described above can be used as it is or as a sugar syrup by appropriately performing decolorization with active carbon, filtration with diatomite, desalting with an ion exchange resin, or concentration with a concentrator, or as a food material by being formed into a powder using a spray dryer or the like. For example, it is used as table sugar as it is, or can also be added to a food or drink such as fermented milk, lactic acid bacteria drink, bread, jam, or confectionery. The addition concentration at that time is not particularly limited and may be appropriately determined in view of flavor, physical properties, or the like. It can also be used in a cosmetic, a pharmaceutical, or the like other than such a food.

Hereinafter, the present invention will be described in more detail with reference to Examples, however, the present invention is by no means limited thereto.

EXAMPLES

Example 1

15 g of lactose of Japanese Pharmacopoeia grade was weighed in a 100 mL Erlenmeyer flask, and 85 g of a Bis-Tris buffer (pH 6.8) that was prepared with deionized water (containing no sodium ions or magnesium ions) was added thereto (lactose concentration: 15%). After lactose was completely dissolved in a boiling water bath, the solution was cooled in a thermostat water tank at 45° C. 2.6 M sodium chloride was added thereto so that the concentration of sodium ions becomes 15 mM, and further 0.75 M magnesium chloride was added thereto so that the concentration of magnesium ions becomes a concentration shown in the following Table 1, and then, GODO-YNL (β-galactosidase derived from *Kluyveromyces lactis*, manufactured by GODO SHUSEI Co., Ltd.) was added at 600 U per gram of lactose, and a reaction was carried out at 40° C. These reaction solutions were subjected to sampling over time until the elapse of 7 hours, and then, the enzyme was inactivated by increasing the temperature to 90° C. in the boiling water bath, and thereafter, the ratio of the residual disaccharide and the tri- or higher galactooligosaccharide was measured by an HPLC analysis under the following conditions. The measurement results when the production amount of the tri- or higher galactooligosaccharide at each magnesium ion concentration reached the maximum are shown in Table 1. Note that in the residual disaccharide, unreacted lactose and a transgalactosylated disaccharide are included.

<HPLC Conditions>
Column: Shodex SUGAR KS-802
Mobile phase: purified water
Flow rate: 0.5 mL/min
Detection: differential refractive index detector

TABLE 1

|  |  | Reaction conditions Na (mM) | | | | | | | |
|---|---|---|---|---|---|---|---|---|---|
|  |  | 15 → | → | → | → | → | → | → | → |
|  |  | Mg (mM) | | | | | | | |
|  |  | 0.0 | 0.1 | 0.5 | 1.0 | 1.5 | 2.0 | 4.0 | 8.0 |
| When tri- or higher galactooligosaccharide content reached maximum | Reaction time (hr) | 7 | 7 | 3 | 3 | 2 | 2 | 2 | 2 |
|  | Residual disaccharide (%) | 60.4 | 33.1 | 29.4 | 27.8 | 33.1 | 32.2 | 33.1 | 30.1 |
|  | Tri- or higher galactooligosaccharide (%) | 9.8 | 13.2 | 13.2 | 13.2 | 13.3 | 13.4 | 13.6 | 13.9 |

Example 2

The procedure was performed in the same manner as in Example 1 except that 2.6 M sodium chloride was added so that the concentration of sodium ions becomes 30 mM, and the ratio of the residual disaccharide and the tri- or higher galactooligosaccharide was measured. The results are shown in Table 2.

TABLE 2

| | | Reaction conditions Na (mM) | | | | | | | |
|---|---|---|---|---|---|---|---|---|---|
| | | 30 | → | → | → | → | → | → | → |
| | | | | | Mg (mM) | | | | |
| | | 0.0 | 0.1 | 0.5 | 1.0 | 1.5 | 2.0 | 4.0 | 8.0 |
| When tri- or higher galactooligo-saccharide content reached maximum | Reaction time (hr) | 7 | 5 | 2 | 2 | 2 | 2 | 2 | 2 |
| | Residual disaccharide (%) | 43.9 | 28.4 | 33.8 | 32.1 | 31.7 | 31.1 | 31.1 | 32.3 |
| | Tri- or higher galactooligo-saccharide (%) | 13.6 | 14.2 | 14.1 | 14.2 | 14.2 | 14.2 | 14.5 | 14.7 |

Example 3

The procedure was performed in the same manner as in Example 1 except that the concentration of lactose in the reaction solution was set to 45%, 2.6 M sodium chloride was added so that the concentration of sodium ions becomes 5 mM, GODO-YNL was added at 250 U per gram of lactose, and a reaction was carried out at 45° C., and the ratio of the residual disaccharide and the tri- or higher galactooligosaccharide was measured. The results are shown in Table 3.

TABLE 3

| | | Reaction conditions Na(mM) | | | | | | | |
|---|---|---|---|---|---|---|---|---|---|
| | | 5 | → | → | → | → | → | → | → |
| | | | | | Mg(mM) | | | | |
| | | 0.0 | 0.1 | 0.5 | 1.0 | 1.5 | 2.0 | 4.0 | 8.0 |
| When tri- or higher galactooligo-saccharide content reached maximum | Reaction time (hr) | 5 | 5 | 3 | 3 | 3 | 3 | 3 | 3 |
| | Residual disaccharide (%) | 30.1 | 35.2 | 32.1 | 31.6 | 31.4 | 31.3 | 31.0 | 31.3 |
| | Tri- or higher galactooligo-saccharide (%) | 18.8 | 18.6 | 18.6 | 18.7 | 19.0 | 19.2 | 19.2 | 19.6 |

Example 4

The procedure was performed in the same manner as in Example 1 except that the concentration of lactose in the reaction solution was set to 45%, 2.6 M sodium chloride was added so that the concentration of sodium ions becomes 60 mM, GODO-YNL was added at 250 U per gram of lactose, and a reaction was carried out at 45° C., and the ratio of the residual disaccharide and the tri- or higher galactooligosaccharide was measured. The results are shown in Table 4.

TABLE 4

| | | Reaction conditions Na (mM) | | | | | | | |
|---|---|---|---|---|---|---|---|---|---|
| | | 60 | → | → | → | → | → | → | → |
| | | | | | Mg (mM) | | | | |
| | | 0.0 | 0.1 | 0.5 | 1.0 | 1.5 | 2.0 | 4.0 | 8.0 |
| When tri- or higher galactooligosaccharide content reached maximum | Reaction time (hr) | 5 | 5 | 3 | 3 | 3 | 3 | 3 | 3 |
| | Residual disaccharide (%) | 31.1 | 35.9 | 33.5 | 32.7 | 32.8 | 32.9 | 32.7 | 32.1 |
| | Tri- or higher galactooligo- saccharide (%) | 24.3 | 23.9 | 24.0 | 24.0 | 24.5 | 24.5 | 24.8 | 25.2 |

From Table 1 and Table 2, it was revealed that by adding magnesium ions so that the concentration becomes 0.5 mM or more when the concentration of sodium ions is 15 mM or 30 mM, the reaction time until the production amount of the tri- or higher galactooligosaccharide reaches the maximum is reduced to half or less as compared with a case where the concentration of magnesium ions is 0 mM or 0.1 mM. Further, it was demonstrated that with the increase in the concentration of magnesium ions, the production amount of the tri- or higher galactooligosaccharide increases. In addition, it was revealed that when the concentration of sodium ions is 15 mM, by adding magnesium ions so that the concentration becomes 1.5 mM or more, the reaction time until the production amount of the tri- or higher galactooligosaccharide reaches the maximum is further reduced. Further, from Table 3 and Table 4, it was revealed that when the concentration of sodium ions is 5 mM or 60 mM, by adding magnesium ions so that the concentration becomes 0.5 mM or more, the reaction time until the production amount of the tri- or higher galactooligosaccharide reaches the maximum is reduced as compared with a case where the concentration of magnesium ions is 0 mM or 0.1 mM, and it was demonstrated that with the increase in the concentration of magnesium ions, the production amount of the tri- or higher galactooligosaccharide increases particularly when the concentration of magnesium ions is 1.5 mM or more.

INDUSTRIAL APPLICABILITY

According to the present invention, the production amount of a tri- or higher galactooligosaccharide can be increased in a short reaction time, and therefore, it is useful as an industrial production method for a galactooligosaccharide.

What is claimed is:
1. A method for producing a galactooligosaccharide, comprising:
allowing a first β-galactosidase derived from a microorganism to react with a substrate to obtain a first-order reaction solution, wherein the substrate is selected from lactose and o-nitrophenyl-β-D-galactopyrano side, glucose, and glycerol; and
then, sequentially a second order reaction allowing a second β-galactosidase different from the first β-galactosidase to react with the first-order reaction solution in the presence of 5 to 60 mM sodium chloride and 0.5 to 8 mM magnesium chloride.
2. The method for producing the galactooligosaccharide according to claim 1, wherein the concentration of magnesium chloride is from 1.5 to 8 mM.
3. The method for producing the galactooligosaccharide according to claim 1, wherein β-galactosidase is derived from a microorganism belonging to the genus *Kluyveromyces*.
4. The method for producing the galactooligosaccharide according to claim 1, wherein the microorganism having β-galactosidase activity in the first-order reaction belongs to the genus *Sporobolomyces*, *Aspergillus*, or *Bacillus*.
5. The method for producing the galactooligosaccharide according to claim 1, wherein the microorganism having β-galactosidase activity in the first-order reaction belongs to the genus *Sporobolomyces*.
6. The method for producing the galactooligosaccharide according to claim 1, wherein the microorganism having β-galactosidase activity in the first-order reaction is *Sporobolomyces singularis*.
7. The method for producing the galactooligosaccharide according to claim 4, wherein the microorganism having β-galactosidase activity in the second-order reaction belongs to the genus *Kluyveromyces*, *Streptococcus*, *Lactobacillus*, *Bifidobacterium*, or *Bacillus*.
8. The method for producing the galactooligosaccharide according to claim 4, wherein the microorganism having β-galactosidase activity in the second-order reaction is *Kluyveromyces lactis*, *Kluyveromyces fragilis*, *Streptococcus thermophilus*, *Lactobacillus bulgaricus*, or *Bifidobacterium breve*.
9. The method for producing the galactooligosaccharide according to claim 4, wherein the microorganism having β-galactosidase activity in the second-order reaction is *Kluyveromyces lactis*.

10. The method for producing the galactooligosaccharide according to claim 1, wherein the microorganism having β-galactosidase activity in the first-order reaction is *Sporobolomyces singularis* and lactose is the substrate, the concentration of lactose is from 10 to 60 mass %, the addition amount of *Sporobolomyces singularis* is from 0.03 to 0.3 U per gram of lactose, the reaction temperature is about 30° C. to 70° C., and the reaction is performed for about 24 hours to 96 hours.

11. The method for producing the galactooligosaccharide according to claim 1, wherein the concentration of residual lactose in the first-order reaction solution is from 5 to 65 mass %, the addition amount of β-galactosidase is from 10 to 1000 U per gram of residual lactose, and the reaction temperature is from 30° C. to 50° C.

\* \* \* \* \*

UNITED STATES PATENT AND TRADEMARK OFFICE
CERTIFICATE OF CORRECTION

PATENT NO. : 11,718,841 B2
APPLICATION NO. : 17/559121
DATED : August 8, 2023
INVENTOR(S) : Ikeda et al.

It is certified that error appears in the above-identified patent and that said Letters Patent is hereby corrected as shown below:

On the Title Page

Item (56), other publications (Line 25), please change "(Na+and K )" to -- (Na+ and K+) --.

In the Claims

Column 12, Line 28 (Claim 1, Line 6), please change "galactopyrano side" to -- galactopyranoside --.

Signed and Sealed this
Thirteenth Day of February, 2024

Katherine Kelly Vidal
*Director of the United States Patent and Trademark Office*